United States Patent [19]

Childress et al.

[11] Patent Number: 5,596,116
[45] Date of Patent: Jan. 21, 1997

[54] PROCESS FOR THE PREPARATION OF SILANE POLYSULFIDES

[75] Inventors: Thomas E. Childress, Newport; Mark P. Bowman, Marietta, both of Ohio

[73] Assignee: OSi Specialties, Inc., Tarrytown, N.Y.

[21] Appl. No.: 526,272

[22] Filed: Sep. 11, 1995

[51] Int. Cl.⁶ .................................................. C08F 7/08
[52] U.S. Cl. ................................. 556/427; 556/428
[58] Field of Search ..................... 556/427, 428

[56] References Cited

U.S. PATENT DOCUMENTS

| | | | |
|---|---|---|---|
| 3,842,111 | 10/1974 | Meyer-Simon et al. | 556/428 |
| 3,946,059 | 3/1976 | Janssen | 556/428 |
| 4,072,701 | 2/1978 | Pletka et al. | 556/428 |
| 4,129,585 | 12/1978 | Buder | 556/428 |
| 4,507,490 | 3/1985 | Panster | 556/427 |
| 4,640,832 | 2/1987 | Bittner | 423/560 |
| 5,399,739 | 3/1995 | French et al. | 556/427 |
| 5,405,985 | 4/1995 | Parker et al. | 556/427 |
| 5,466,848 | 11/1995 | Childress | 556/427 |

Primary Examiner—Mark D. Sweet

[57] ABSTRACT

Sulfur-containing organosilicon compounds useful as coupling agents in vulcanizable rubbers to enhance various properties, including low rolling resistance for automobile tires, are prepared. Preferred compounds include $\Omega$, $\Omega'$-bis (trialkoxysilylalkyl) polysulfides. In one embodiment, the reaction product of ethanolic sodium ethoxide and elemental sulfur is reacted with chloropropyltriethoxysilane. Alternatively, sodium metal is reacted with a mixture of ethanol and elemental sulfur, and then chloropropyltriethoxysilane. The use of sodium metal alcoholates provides an efficient and economical process.

16 Claims, No Drawings

PROCESS FOR THE PREPARATION OF SILANE POLYSULFIDES

TECHNICAL FIELD

The invention is directed to the preparation of sulfur-containing organosilicon compounds useful as coupling agents in vulcanizable rubbers to enhance products made from them. In its preferred form, the invention improves the preparation of $\Omega,\Omega'$-bis (trialkoxysilylalkyl) polysulfides.

Sulfur-containing organosilicon compounds have found widespread use in a variety of rubber products in the last two decades. Uses include tire walls and bodies, rubber hoses, rubber belts, and numerous other rubber products. Depending on the formulation, selected properties of the rubber can be modified.

Since the early 1980's, automobile manufacturers have been encouraging the production of low-rolling-resistance tires. A number of sulfur-containing organosilicon compounds have been identified as useful in this regard. The improvements obtainable could be helpful in meeting federal fuel economy standards without sacrificing wet traction and wear. Silane polysulfide coupling agents, such as 3,3'-bis (triethoxysilylpropyl) tetrasulfide, have been proposed for use in low-rolling-resistance tires.

To achieve optimum effect, it has been found that each low-rolling-resistance tire should contain several ounces of this or another suitable silane.

There is a need for new processes to produce organosilane polysulfides effective for use in low-rolling-resistance tires, and other uses, in good yield to permit economical production of large quantities with controllable safety and environmental impact.

BACKGROUND ART

The art of manufacturing organosilane polysulfides is well established, with the art offering a variety of processing strategies.

Meyer-Simon, Schwarze, Thurn, and Michel disclose the reaction of a metal polysulfide with an $\Omega$-chloroalkyltrialkoxysilane in U.S. Pat. No. 3,842,111. Examples 2 and 3 disclose the preparation of 3,3'-bis (triethoxysilylpropyl) tetrasulfide by reacting $Na_2S_4$ with 3-chloropropyltriethoxysilane in water-free alcohol. A procedure for preparing the metal polysulfide is not exemplified.

In U.S. Pat. No. 4,072,701, Pletka describes the preparation of these compounds by first heating 3-chloropropyltrichlorosilane (Example 1) with ethanol, and then adding both sulfur and NaSH. The reaction developed gaseous hydrogen sulfide in situ, but some of the sulfur therein was not recoverable (see, U.S. Pat. No. 4,129,585, col. 1, lines 32–34, in this regard). Therefore, the yields based on added sulfur tended to be low. Also, the use of NaSH is problematic due to its deliquescent nature and its tendency to oxidize to sulfate. The deliquescence is troublesome from the standpoint that it increases the risk that water will enter the reaction and cause hydrolysis of the alkoxide reactants.

After describing the above two patents in U.S. Pat. No. 4,129,585, Buder, Pletka, Michel, Schwarz and Düsing, describe a procedure for making the noted compounds without the production of gaseous hydrogen sulfide. The process entails reacting a suitable alkali metal alcoholate, e.g., sodium ethoxide, in preferably alcoholic solution with a desired $\Omega$-chloroalkyltrialkoxysilane and then adding a suitable metal hydrogen sulfide and sulfur. The resulting product was purified by separating the salt formed and distilling off the alcohol. Although the preferred process employed powdered hydrosulfide, the use of the metal hydrogen sulfide can be a source of water entering the system unless precautions are taken. French and Lee also disclosed a process that employed an alkali metal hydrogen sulfide such as NaSH in a separate step (U.S. Pat. No. 5,399,739).

In U.S. Pat. No. 4,507,490, Panster, Michel, Kleinschmidt and Deschler, first prepare $Na_2S$. Again, they employ a metal hydrogen sulfide but react it with an alkali metal, such as sodium, in a polar solvent, such as ethanol. This reaction is highly exothermic and evolves hydrogen gas. The process is said to eliminate the use of an alkali metal alcoholate solution, noting that its production requires such a great deal of time as to be industrially improbable. The $Na_2S$ is reacted with additional sulfur to form a desired polysulfide, preferably $Na_2S_4$. The polysulfide is then reacted with a desired $\Omega$-chloroalkyl trialkoxysilane, e.g., $Cl(CH_2)_3Si(OC_2H_5)_3$, to form the desired $\Omega,\Omega'$-bis (trialkoxysilylalkyl) polysulfide.

In U.S. patent application Ser. No. 08/314,204 by Childress (filed Sep. 28, 1994), silane polysulfides are prepared by contacting hydrogen sulfide gas with an active metal alkoxide solution to form a first intermediate product, reacting the first intermediate product with elemental sulfur to form a second intermediate product, and then reacting the second intermediate product with a halohydrocarbylalkoxysilane. In a continuation-in-part, Childress, et al., simplify this process somewhat by combining the first two steps in U.S. patent application Ser. No. 08/383,480 (filed Feb. 2, 1995); hydrogen gas is contacted with an active metal alkoxide and the intermediate product reacted with elemental sulfur and a halohydrocarbylalkoxysilane.

Janssen and Steffen, in U.S. Pat. No. 3,946,059, offer a distinct approach and criticize procedures of the type described above. They eliminate the production, and therefore separation, of salts formed in the above reactions by contacting a bis (alkylalkoxysilyl) disulfide with sulfur at a temperature between 100° and 200° C. This procedure, however, adds the difficulty of the high temperature processing and requires the initial preparation of bis-silyl disulfides by the reaction of sulfuryl chloride with silyl mercaptans. Parker, et al., also disclosed a somewhat complicated process involving a phase transfer catalyst and an aqueous phase (U.S. Pat. No. 5,405,985).

While the possibility might appear to exist that commercial forms or alkali metal sulfides, e.g., sodium tetrasulfide, could be employed, this would not be practical. The commercial forms of sodium tetrasulfide include water which must be completely removed prior to contact with the alkoxylates. If water is present, the alkoxide is hydrolyzed and a polysiloxane polymer is formed. And, while Bittner, et al. disclose in U.S. Pat. No. 4,640,832, the reaction of elemental sodium and sulfur to form polysulfides, this route has certain economic and practical limitations. Reaction temperatures are high; for formation of $Na_2S_3$ or $Na_2S_4$, for example, the reaction is preferably run at 340° to 360° C. At these temperatures, the polysulfides are corrosive so that choosing an appropriate reactor is imperative; costly alloys of aluminum and magnesium are suggested, as is the use of glassy carbon.

Thus, the prior art has found the generation of hydrogen sulfide gas, the separation of sodium chloride, the preparation of metal alkoxylates, and development of appropriate reaction conditions to be problematic in the preparation of sulfur-containing organosilicon compounds, and did not recognize that there was possible a reaction scheme which efficiently and effectively combines all of them. The invention provides a process which combines these and still obtains high yields based on sulfur.

The prior art also did not recognize that there are numerous possible reaction schemes which avoid the use of either hydrogen sulfide gas or metal hydrogen sulfides, and which provide the desired silane polysulfides efficiently and effectively. These schemes involve process variants with fewer steps than taught by the prior art, with concurrent economic advantages in terms of reduced production times. The invention also provides alternative processes employing these schemes which obtain high yields based on sulfur.

SUMMARY OF THE INVENTION

It is an object of the invention to provide improved processes for preparing sulfur-containing organosilicon compounds useful as coupling agents in vulcanizable rubbers.

It is a further object of a preferred aspect of the invention to provide improved processes for preparing $\Omega,\Omega'$-bis (trialkoxysilylalkyl) polysulfides useful in the preparation of a variety of rubber products, specifically including low-rolling-resistance tires.

It is a further and more specific object of the invention to prepare 3,3'-bis (triethoxysilylpropyl)tetrasulfide economically in high yield.

These and other objects are achieved by the invention which provides two processes for preparing silane polysulfides, one process comprising:

(a) reacting an active metal alkoxide solution in alcohol with elemental sulfur, and (b) reacting the product of step (a) with a halohydrocarbylalkoxysilane of the formula Q—R—X in which Q is

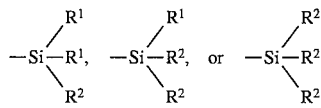

and in which $R^1$ is an alkyl group of 1 to 4 carbon atoms or phenyl, and $R^2$ is an alkoxy group with 1 to 8, preferably 1 to 4, carbon atoms,
a cycloalkoxy group including 5 to 8 carbon atoms, or
a straight or branched chain alkylmercapto group with 1 to 8 carbon atoms, wherein the various $R^1$ and $R^2$ groups can be the same or different, R is a divalent hydrocarbyl group including 1 to 18 carbon atoms, and X is a halogen, to produce a compound of the formula Q—R—$S_n$—R—Q in which Q and R are as defined above, and n is an integer of from 1 to 9, preferably from 2 to 5.

Alternatively, in step (a) sodium metal is added directly to a slurried mixture of an alcohol and elemental sulfur, and the product is reacted with a halohydrocarbylalkoxysilane Q—R—X, to produce a compound of the formula Q—R—$S_n$—R—Q, wherein Q, R, X, and n are as defined above.

The two processes combine, in differing forms, the primary reactants sodium metal, alcohol, elemental sulfur, and halohydrocarbylalkoxysilane Q—R—X, to produce a compound of the formula Q—R—$S_n$—R—Q, wherein Q, R, X, and n are as defined above. In one embodiment, sodium metal and alcohol are prereacted to form sodium alkoxide, and the product is reacted with elemental sulfur before reacting with the halohydrocarbylalkoxysilane. In the other, sodium metal is added to a slurry of alcohol and sulfur before reacting with the halohydrocarbylalkoxysilane.

In preferred embodiments, the desired product is 3,3'-bis (triethoxysilylpropyl) tetrasulfide, represented by the formula

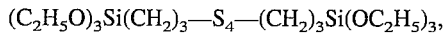

and is prepared by coreacting appropriate amounts of an ethanol solution of sodium ethoxide with elemental sulfur, followed by $Cl(CH_2)_3Si(OC_2H_5)_3$ addition and reacting to completion, or by the reaction of sodium metal with a slurried mixture of appropriate amounts of ethanol and elemental sulfur, followed by $Cl(CH_2)_3Si(OC_2H_5)_3$ addition, and reacting to completion. Either process produces the preferred product $(C_2H_5O)_3Si(CH_2)_3S_4(CH_2)_3Si(OC_2H_5)_3$, which is indistinguishable from that produced by prior art processes, by gas chromatographic or elemental sulfur analyses.

All parts and percentages in this description are on a weight basis and are based on the weight of the composition at the referenced stage of processing.

By the use of the processes of the invention, silane polysulfides of high quality are prepared efficiently and in good yield.

DETAILED DESCRIPTION

The invention, which relates to the preparation of sulfur-containing organosilicon compounds useful for a variety of purposes, especially as coupling agents in vulcanizable rubbers, will be described with special reference to the preparation of a preferred class of compounds, the $\Omega,\Omega'$-bis (trialkoxysilylalkyl) polysulfides.

Among this class of compounds are a wide number of materials, including the various polysulfides listed below wherein the term polysulfide includes all of the di, tri, tetra, penta, hexa, hepta, octa, and nona-sulfides according to the following formulae:

bis (trimethoxysilylmethyl) polysulfides, bis (triethoxysilylmethyl) polysulfides, bis (dimethylethoxysilylmethyl) polysulfides, bis (tripropoxy-silylmethyl) polysulfides, bis (tributoxysilylmethyl) polysulfides, bis (tripentoxy-silylmethyl) polysulfides, bis (trihexoxysilylmethyl) polysulfides, bis (triheptoxy-silylmethyl) polysulfides, and bis (trioctyloxysilylmethyl) polysulfides;

3,3'-bis (trimethoxysilylpropyl) polysulfides, 3,3'-bis (triethoxysilylpropyl) polysulfides, 3,3'-bis (dimethylethoxysilylpropyl) polysulfides, 3,3'-bis (tripropoxysilylpropyl) polysulfides, 3,3'-bis (tributoxysilylpropyl) polysulfides, 3,3'-bis (tripentoxysilylpropyl) polysulfides, 3,3'-bis (trihexoxysilylpropyl) polysulfides, 3,3'-bis (triheptoxysilylpropyl) polysulfides, 3,3'-bis (trioctyloxysilylpropyl) polysulfides and 3,3'-bis (methyldiethoxysilylpropyl) polysulfides;

4,4'-bis (trimethoxysilylbutyl) polysulfides, 4,4'-bis (triethoxysilylbutyl) polysulfides, 4,4'-bis (dimethylethoxysilylbutyl) polysulfides, 4,4'-bis (tripropoxysilylbutyl) polysulfides, 4,4'-bis (tributoxysilylbutyl) polysulfides, 4,4'-bis (tripentoxysilylbutyl) polysulfides, 4,4'-bis (trihexoxysilylbutyl) polysulfides, 4,4'-bis (triheptoxysilylbutyl) polysulfides, and 4,4'-bis (trioctyloxysilylbutyl) polysulfides;

5,5'-bis (trimethoxysilylpentyl) polysulfides, 5,5'-bis (triethoxysilylpentyl) polysulfides, 5,5'-bis (dimethylethoxysilylpentyl) polysulfides, 5,5'-bis (tripropoxy-silylpentyl) polysulfides, 5,5'-bis (tripentoxysilylpentyl) polysulfides, 5,5'-bis (tripentoxysilylpentyl) polysulfides, 5,5'-bis (trihexoxysilylpentyl) polysulfides; and 5,5'-bis (triheptoxysilylpentyl) polysulfides, and 5,5'-bis (trioctyloxysilylpentyl) polysulfides.

Similarly, the 6,6'-bis (trialkoxysilylhexyl) polysulfides; the 7,7'-bis (trialkoxysilylheptyl) polysulfides; the 8,8'-bis (trialkoxysilyloctyl) polysulfides; the 9,9'-bis (trialkoxysilylnonyl) polysulfides; the 10,10'-bis (trialkoxysilyldecyl) polysulfides; and the isomers of these are included. Indeed, this disclosure is meant to include, each of the individual compounds comprised of combinations of the various groups encompassed by the generic formula

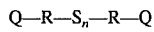

wherein, Q, R and n are as defined above.

It is recognized by those skilled in the art that silane polysulfides wherein n is defined as an integer, e.g., 4, are in fact mixtures of distinct polysulfides wherein n has a range of values which average to 4. Correspondingly, silane polysulfides wherein n is a low number such as 2 will in fact contain silanes where n may equal 1. While such silanes are technically not polysulfides, they are intended to be included as products of the processes of the invention.

This description illustrates the production of the preferred compound, 3,3'-bis (triethoxysilylpropyl) tetrasulfide:

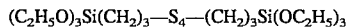

by the processes described above. At times in the following description, Et is used to designate an ethyl group and Me is used to designate a methyl group.

Preparation of the Active Metal Alkoxide

As noted above, the processes can be used to prepare a large number of end products. For each of these it is necessary to start with an active metal and an alcohol. They may be prereacted to form an active metal alkoxide solution in one embodiment. The active metal alkoxide will have the formula M—$R^2$, wherein M represents an active metal and $R^2$ is as defined above. Among the preferred active metals are those of the alkali metal group, especially sodium and potassium. The most preferred is sodium. However, among the other metals useful are lithium, rubidium and cesium. Among the preferred alkoxides are those containing methoxy, ethoxy, n-propoxy, i-propoxy, n-butoxy, i-butoxy, 2-methoxyethoxy or 2-ethoxyethoxy groups.

The prereaction, if performed, is carried out in a suitable organic solvent compatible with the alkoxide. In principle, any polar organic solvent can be employed that reacts with neither the alkali or other metal nor with the organic silicon compounds to form an undesired byproduct.

Preferably, the organic solvent is a linear or branched alcohol having 1 to 5 carbon atoms, e.g., methyl, ethyl, propyl, butyl or pentyl alcohol, as well as iso-propyl alcohol, iso-butyl alcohol and 2-methoxyethanol. Also suitable are cycloalkyl alcohols having 5 to 8 carbon atoms, e.g., cyclopentyl alcohol, cyclohexyl alcohol, cyclooctyl alcohol, phenyl or benzyl alcohol. It is useful to employ the alcohol which in each case corresponds to the $R^2$ group. In a given case, advantageously there can also be used a mixture of these alcohols, e.g., when different $R^2$ groups are used in a compound. Particularly preferred are methanol and ethanol, preferably in absolute form. In one preferred process, sodium metal is reacted with ethanol to form an ethanolic solution of sodium ethoxylate.

The reaction of active metal, e.g., sodium metal, and a suitable alcohol, e.g., ethanol, is preferably conducted with an excess of alcohol to produce a metal alkoxide, e.g., sodium ethoxide, solution. The following equation summarizes the reaction:

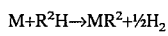

The sodium or other metal should be maintained free of contact with moisture. The manufacture of sodium methoxide has been described by Arend (Arend, A. G., *Perfumery Essent. Oil Record*, 28, 372–75, 1947). The preferred sodium ethoxide reaction is similar, but slower than the sodium methoxide reaction.

The concentration of the sodium ethoxide solution may be as low as about 10 wt % and as high as its solubility limit, which is about 25 wt % at 25° C. A high concentration of sodium ethoxide is desirable, since better product yields for given reactor size are obtained. The typical concentration for commercially-available sodium ethoxide is about 21 wt %.

Sulfur Addition and Reaction with Ethoxide

The ethoxide reaction mixture is cooled, e.g., to about 25° C., then sulfur, preferably in powdered form, is added to the reactor in an amount sufficient to form a desired active metal polysulfide intermediate. When the sulfur addition is complete, the reactor is reheated, e.g., to about 45° C. During this period, the system is preferably maintained at atmospheric pressure under a nitrogen blanket. It is preferred to maintain agitation in the reactor after the sulfur addition, sufficient to insure solubilization and reaction. It is also preferred, during and after the sulfur addition, to keep air out of the kettle to avoid oxidation which may contribute to a darkening of product color.

Reaction of Sodium with Ethanol and Sulfur

In an alternate process, ground sulfur is slurried in an alcohol such as ethanol and sodium is slowly added using equipment like that described above. The system temperature is generally maintained between about 75° C. and 80° C., and typically the reactor is cooled periodically to room temperature to allow the sodium to be added. It is preferred to keep air out of the kettle and agitate as described above.

Halohydrocarbyltrialkoxysilane

The process of the invention employs a halohydrocarbyltrialkoxysilane for reaction with the polysulfide products formed by reaction of sodium ethoxide with sulfur, or sodium, ethanol, and sulfur. These compounds meet the general formula Q—R—X in which Q and R are as defined above and X is a halogen, typically chlorine, but bromine, iodine and fluorine compounds can be effective. In this formula, and therefore also in the final product, the hydrocarbyl group R signifies methylene as well as preferably n-propylene, i-butylene, or n-butylene, but can also be n-pentylene, 2-methylbutylene, 3-methylbutylene, 1,3-dimethylpropylene, n-hexylene, or n-decylene.

Illustrative compounds within formula Q—R—X are 3-chloropropyltriethoxysilane, 3-bromopropyltriethoxysilane, chloromethyltrimethoxysilane, 3-chloropropyltrimethoxysilane, 3-chloropropyldiethoxymethylsilane, 3-chloropropylcyclohexoxydimethylsilane, 4-bromobutyldiethoxybenzylsilane, 4-chlorobutyltrimethoxysilane, 5-chloropentyldimethoxyphenylsilane, 3-bromo-i-butyltriethyoxysilane, 3-chloropropyldimethoxy-p-ethylphenylsilane, 3-chloropropylethoxymethylethylsilane, 5-chloro-n-pentyldiethoxycyclopentylsilane, 3-bromopropyldimethoxycyclopentoxysilane, 3-bromo-2-methylpropyldimethoxy-cyclooctylsilane, 3-chloropropyldiethoxy-2-methoxyethoxy-silane, 3-chloropropyldibutoxymethylsilane, 3-bromopropylphenyloxydimethoxysilane, 3-chloropropyldi-i-butoxy-2-methylphenylsilane, 4-chlorobutyldimethoxybenzyloxysilane, 3-chloropropyltributoxysilane, 3-chloropropyldiethoxyamylsilane, and 3ochloropropyldiethoxy-p-methylphenylsilane.

Again here, as in the case of the inclusion of compounds meeting the definition of the formula for the end products, this disclosure is meant to include each of the individual compounds comprised of combinations of the various groups encompassed by the generic formula Q—R—X in which Q, R and X are as defined above.

In one preferred embodiment of the invention, a chloroalkylalkoxysilane is used as the reactant. The chloroalkylalkoxysilane can be purchased or prepared according to any of the techniques available to those of ordinary skill in the art. One preferred practice is to prepare it by transesterification of $Cl(CH_2)_3Si(OMe)_3$.

In an alternative embodiment of the invention, the methoxy ester can be employed to form 3,3'-bis (trimethoxyalkoxysilane) polysulfide, and this product can then be converted to the ethyl or higher ester by transesterification in situ.

According to this embodiment, $Cl(CH_2)_3Si(OEt)_3$ can be prepared by the following transesterification reaction, typically at a temperature of from about 70° to about 100° C. and atmospheric pressure using about 2000 ppm paratoluenesulfonic acid:

$$Cl(CH_2)_3Si(OMe)_3 + 3\ EtOH \rightarrow Cl(CH_2)_3Si(OEt)_3 + 3\ MeOH$$

This reaction is preferably run by continuously feeding ethanol while removing by-product methanol from the system to drive the equilibrium toward chloropropyltriethoxysilane. The reaction can conveniently begin at atmospheric pressure and reflux temperatures, i.e., a pot temperature of from about 80° to about 100° C. At the end of the reaction, the excess ethanol can be stripped off using vacuum and a somewhat higher temperature. A typical final condition for the ethanol strip would be a temperature of about 120° C. and a pressure of about 100 mm Hg.

Coreaction of Active Metal Alkoxide with Elemental Sulfur and with Halohydrocarbyltrialkoxysilane In this embodiment of the process, the active metal alkoxide solution is combined with the elemental sulfur, and the halohydrocarbyltrialkoxysilane is then added at about 70° to 80° C., e.g., at reflux, typically over about 3 hours, with reflux being maintained for about 1 to 3 hours, followed by cooling to about 25° C. The desired reaction, for the preferred product, is:

$$2\ NaOEt + 4\ S + 2\ Cl(CH_2)_3Si(OEt)_3 \rightarrow (EtO)_3Si(CH_2)_3S_4—(CH_2)_3Si(OEt)_3$$

The chloropropyltriethoxysilane is preferably added at a rate such that the entire quantity is charged in a time period of over about 1 hour, preferably about 3 hours. If the duration is less than one hour, excessive chloropropyltriethoxysilane can accumulate in the reactor. Salt particles are formed during the reaction, and it is preferred to employ sufficient reactor agitation to maintain these in suspension. When the addition of the chloropropyltriethoxysilane is complete, the reactor is preferably heated to about 80° C. and held under reflux for a suitable time, e.g., from about 1 to about 3 hours, typically about 1.5 hours. After this period of reflux, the reactor is immediately cooled, e.g., to about 25° C. as mentioned above.

Reaction of Sodium Metal with Mixed Alcohol, Elemental Sulfur and Halohydrocarbyltrialkoxysilane Alternatively, excess alcohol and elemental sulfur are combined in slurry form, followed by the intermittent addition of pieces of sodium metal, and followed by addition of halohydrocarbylalkoxysilane. For the preferred product, the desired reaction is:

$$2\ Na + 2\ EtOH + 4\ S + 2\ Cl(CH_2)_3Si(OEt)_3 \rightarrow (EtO)_3Si(CH_2)_3S_4(CH_2)_3Si(OEt)_3$$

The reaction is run at about 40° to 45° C., and the first step is accompanied by the generation of hydrogen gas, for which safe handling considerations must be made. When the addition of sodium metal is complete as evidenced by cessation of gas evolution and the addition of chloropropyltriethoxysilane is complete, the reaction is heated to about 80° C., i.e., reflux, for about 1 to about 3 hours, followed by cooling to about 25° C.

Salt Removal

The reaction by either process produces the desired product and also produces salt. In the preferred reaction, sodium chloride salt produced in the chloropropyltriethoxysilane addition step can be removed by filtering or centrifuging. If filtration is used, the media pore size should be about 5μ. Typically, no filter aid is necessary since the average particle size is fairly large, but one can be employed if needed. If centrifuging is employed, a basket or continuous scroll-type device can be employed.

The resulting filtercake will contain residual liquid product and can be washed, e.g., with ethanol to improve overall product yield.

Solvent Strip

Either process preferably includes a step of stripping off detrimental levels of solvent, preferably reducing the solvent concentration to less than about 5% by weight. Assuming an ethanol wash has not been used, the crude product can contain as much as 60 wt % ethanol. Stripping, preferably in a single stage, can be employed to yield a product containing less than about 2 wt % ethanol. One suitable stripping technique is batch stripping of the crude material in a reactor, e.g., to a final condition of 100° C. and 50 mm Hg absolute pressure. A small quantity of salt may precipitate out during the ethanol strip, and it is preferred to subject the product to a final filtration as necessary to remove this.

EXAMPLES

The following examples are presented for the purpose of further illustrating and explaining the invention, and are not to be taken as limiting in any regard. Unless otherwise indicated, all parts and percentages are based on the weight of the components at the indicated stage of processing.

Example 1

This example describes the preparation of the preferred end product, 3,3'- bis (triethoxysilylpropyl) tetrasulfide by reaction of active metal alkoxide with elemental sulfur and then chloropropyltriethoxysilane.

Preparation of Sodium Ethoxide

To a 500 ml glass reactor equipped with a feed funnel, a reflux column, a fritted glass sparge tube and thermometer, 13.97 grams of dry sodium chunks were added. The reactor and the column were then purged with $N_2$ for >5 minutes. Afterwards, 188.33 grams of ethanol was charged into the feed funnel. During this step, the ethanol was added slowly enough to prevent the sodium from melting. After 85 minutes, all of the sodium was dissolved and the reactor was cooled from about 90° C. to about 40° C.

Preparation of Chloropropyltriethoxysilane

Chloropropyltrimethoxysilane was separately transesterified to the ethyl ester, chloropropyltriethoxysilane, in a 1 liter glass reactor equipped with a heating mantle, thermometer, ethanol addition funnel and a 5 tray, 1 inch diameter glass Oldershaw column. This column should have at least about 3 theoretical trays.

The reactor was initially charged with 527.15 grams of chloropropyltrimethoxysilane, 1.05 grams of p-toluenesulfonic acid (2000 ppm), and 130 grams of ethanol. During the first part of the reaction the reactor temperature was run in the range 80°–90° C. Then the ethanol feedrate was cut back and the reactor was run at 98°–115° C., to help drive MeOH out of the reactor. A reflux ratio of about 8:1 was used for the entire run. The ethanol usage was 2.3 times the theoretical amount. The reaction was run for about 8.9 hours, over a two day period. High temperature (111° C.) at the end of the run helped assure a relatively low residual ethanol concentration, i.e., 6.7%. This material could be vacuum stripped to reduce the ethanol further.

| PRODUCT ANALYSIS BY GAS CHROMATOGRAPHY | |
| --- | --- |
| Ethanol | 6.7 area % |
| Chloropropylmethoxydiethoxysilane | 1.02 area % |
| Chloropropyltriethoxysilane | 90.7 area % |

Reaction of Sodium Ethoxide/Sulfur with Chloropropyltriethoxysilane

First, 162 grams of 21% sodium ethoxide solution in ethanol were charged to a 500 ml glass reactor equipped with a feed funnel, a reflux column, fritted glass sparge tube, and thermometer. Next, 32.1 grams of sulfur were added to the reactor. Then the reactor was heated to 75° C. and 120.4 grams of chloropropyltriethoxysilane were added over a 50 minute period. During this addition, the reactor temperature was maintained between 69° C. and 83° C. After the addition, the reactor was held at 70° C. for 16 hours.

When the reactor contents were analyzed by gas chromatography, normalized for 53% ethanol content (note that the crude product had not been stripped), the product composition was virtually identical to commercially available product and that produced by the process disclosed in U.S. application Ser. No. 08/314,204 cited above.

Example 2

Reaction of Sodium/Ethanol/Sulfur Product with Chloropropyltriethoxysilane

Using equipment analogous to that used in Example 1 above, 189.2 grams ethanol and 39.7 grams of ground sulfur were added to a 500 ml glass reactor. The reactor was equipped with a heating mantle, agitator, reflux column and thermometer. To the ethanol-sulfur slurry, 14.3 grams of sodium was added in small chunks over a 6.2 hour period. During most of the reaction, the system temperature was maintained between 75° C. and 80° C. However, the reactor was periodically cooled to room temperature to allow the sodium chunks to be added. After the sodium was added, the reactor was heated to reflux (about 81° C.) and held for 1.1 hours. At this time, the reactor contents were dark brown. A portion of the reactor contents (24.9 grams) was removed for further study, and not included in calculating the needed amount of chloropropyltriethoxysilane.

Next, 137.2 grams of chloropropyltriethoxysilane was added to the reactor contents over a 50 minute period. During this time, the reactor temperature was maintained at 44° to 49° C. Next, the reactor was heated to reflux (about 79.5° C.) and held for about 1.6 hours.

The reactor contents, which were dark brown, were analyzed by gas chromatography. When normalized for its 51% ethanol content (note that the crude product was not stripped), the product composition was very similar to that obtained above.

Example 3

Reaction of $Na_2S$/Chloropropyltriethoxysilane Product with Sulfur

This comparative example illustrates the surprising results applicants achieve using the process of their invention as well as the importance of the ordered addition of reactants in applicants' claimed process.

In equipment analogous to that used above, a solution of $Na_2S$ in ethanol was prepared as above from 260.7 grams of 21% sodium ethoxide in ethanol and 12.6 grams of $H_2S$ gas. The solution was heated to reflux and 182.4 grams of chloropropyltriethoxysilane was added over a 1 hour period. After cooling to 25° C., 35.6 grams of sulfur was added, and heat applied to reflux within 30 minutes, followed by heating at reflux for 90 minutes. After filtration, gas chromatographic analysis of the unstripped product showed the major non-solvent component to be monosulfide, $(EtO)_3Si(CH_2)_3S—(CH_2)_3Si(OEt)_3$, with significant unreacted chloropropyltriethoxysilane. The unfiltered reaction mixture contained unreacted sulfur as well as the expected salt.

The above description is for the purpose of teaching the person of ordinary skill in the art how to practice the present invention and it is not intended to detail all of those obvious modifications and variations of it which will become apparent to the skilled worker upon reading the description. It is intended, however, that all such obvious modifications and variations be included within the scope of the present invention which is defined by the following claims. The claims cover the indicated components and steps in all arrangements and sequences which are effective to meet the objectives intended for the invention, unless the context specifically indicates the contrary.

We claim:

1. A process for the preparation of silane polysulfides without the use of hydrogen sulfide comprising:
   (a) obtaining an intermediate product by reacting a metal alkoxide in alcohol with elemental sulfur, or by reacting sodium metal with elemental sulfur and an alcohol, and
   (b) reacting the intermediate product of step (a) with a halohydrocarbylalkoxysilane of the formula Q—R—X in which Q is

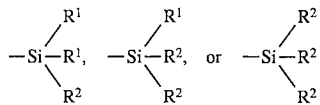

and in which
   $R^1$ is an alkyl group of 1 to 4 carbon atoms or phenyl, and
   $R^2$ is an alkoxy group with 1 to 8, preferably 1 to 4, carbon atoms,
       a cycloalkoxy group including 5 to 8 carbon atoms, or a straight or branched chain alkylmercapto group with 1 to 8 carbon atoms,
       wherein the various $R^1$ and $R^2$ groups can be the same or different,
   R is a divalent hydrocarbyl group including 1 to 18 carbon atoms, and
   X is a halogen,
   to produce a compound of of the formula Q—R—$S_n$—R—Q
   in which Q and R are as defined above, and n is an integer of from 1 to 9.

2. A process according to claim 1 wherein the silane polysulfide is purified to remove salt and solvent.

3. A process according to claim 1 wherein the products of the last reaction step are methoxy derivatives, and said methoxysilane derivatives are converted to silane derivatives containing higher alkoxy groups.

4. A process according to claim 1 wherein Q is

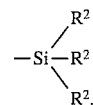

5. A process according to claim 1 wherein $R^2$ is ethoxy.

6. A process according to claim 1 wherein n is within the range of from 2 to 5.

7. A process according to claim 1 wherein the active metal alkoxide is sodium ethoxylate.

8. A process according to claim 1 wherein the halogen is chlorine.

9. A process according to claim 1 wherein R is 1,3-propylene.

10. A process for the preparation of $(C_2H_5O)_3Si(CH_2)_3$—$S_4$—$(CH_2)_3Si(OC_2H_5)_3$, without the use of hydrogen sulfide comprising:
    (a) reacting a mixture of an ethanol solution of sodium ethoxide with elemental sulfur, and
    (b) reacting the product of step (a) with $Cl(CH_2)_3Si(C_2H_5O)_3$ to completion.

11. A process according to claim 10 wherein sodium ethoxylate is formed by reacting sodium with ethanol.

12. A process according to claim 10 wherein salts formed in the reaction are filtered off and the solvents stripped off after the reaction is completed.

13. A process for the preparation of $(C_2H_5O)_3Si(CH_2)_3$—$S_4$—$(CH_2)_3Si(OC_2H_5)_3$, comprising:
    (a) reacting sodium metal with a mixture of ethanol and elemental sulfur, and
    (b) reacting the product of step (a) with $Cl(CH_2)_3Si(C_2H_5O)_3$ to completion.

14. A process according to claim 13 wherein the mixture of ethanol and elemental sulfur is a slurry.

15. A process according to claim 14 wherein the sodium metal is added slowly and the reaction mixture is intermittently cooled during the sodium addition.

16. A process according to claim 13 wherein salts formed in the reaction are filtered off and the solvents stripped off after the reaction is completed.

* * * * *